US010004411B2

(12) United States Patent
Chen et al.

(10) Patent No.: US 10,004,411 B2
(45) Date of Patent: Jun. 26, 2018

(54) LIVING BODY DETERMINATION DEVICES AND METHODS

(71) Applicant: MediaTek Inc., Hsin-Chu (TW)

(72) Inventors: Tung-Chien Chen, Taipei (TW); Yu-Ting Chen, Taipei (TW)

(73) Assignee: MEDIATEK INC., Hsin-Chu (TW)

( * ) Notice: Subject to any disclaimer, the term of this patent is extended or adjusted under 35 U.S.C. 154(b) by 0 days. days.

(21) Appl. No.: 14/905,694

(22) PCT Filed: May 15, 2015

(86) PCT No.: PCT/CN2015/079024
§ 371 (c)(1),
(2) Date: Jan. 15, 2016

(87) PCT Pub. No.: WO2015/172736
PCT Pub. Date: Nov. 19, 2015

(65) Prior Publication Data
US 2016/0150986 A1 Jun. 2, 2016

Related U.S. Application Data

(60) Provisional application No. 62/134,110, filed on Mar. 17, 2015, provisional application No. 61/994,237, filed on May 16, 2014.

(51) Int. Cl.
G06K 9/00 (2006.01)
A61B 5/024 (2006.01)
(Continued)

(52) U.S. Cl.
CPC ........ *A61B 5/02416* (2013.01); *A61B 5/0013* (2013.01); *A61B 5/0037* (2013.01);
(Continued)

(58) Field of Classification Search
CPC ................. G06K 9/00; A61B 5/00; G06T 7/00
USPC ........... 382/128–134, 276, 13; 600/407, 410, 600/411, 477, 508
See application file for complete search history.

(56) References Cited

U.S. PATENT DOCUMENTS 7,547,283 B2 * 6/2009 Mourad ................. A61B 5/031
600/459
8,542,878 B2 9/2013 Cennini et al.
(Continued)

FOREIGN PATENT DOCUMENTS

| CN | 102341811 A | 2/2012 |
| CN | 102499664 A | 6/2012 |

(Continued)

OTHER PUBLICATIONS

International Search Report dated Aug. 3, 2015, issued in application No. PCT/CN2015/079024.
(Continued)

*Primary Examiner* — Abolfazl Tabatabai
(74) *Attorney, Agent, or Firm* — McClure, Qualey & Rodack, LLP

(57) ABSTRACT

A measurement apparatus and method for measuring a vital sign of a subject are provided. A plurality of frames showing a subject is captured. A region of interest (ROI) on the subject is detected. A vital-sign signal is generated according to the sensing signals related to the ROI. A quality index of the vital-sign signal is evaluated. Whether the subject is a living body is determined according to the quality index. A determination result of determining whether the subject is the living body is used to control a heart-rate measurement operation.

17 Claims, 12 Drawing Sheets

(51) Int. Cl.
| | |
|---|---|
| *G06T 7/00* | (2017.01) |
| *A61B 5/00* | (2006.01) |
| *A61B 5/11* | (2006.01) |
| *G06K 9/46* | (2006.01) |
| *G06T 5/00* | (2006.01) |
| *G06T 7/90* | (2017.01) |
| *A61B 5/02* | (2006.01) |

(52) U.S. Cl.
CPC ...... *A61B 5/02427* (2013.01); *A61B 5/02444* (2013.01); *A61B 5/1128* (2013.01); *A61B 5/742* (2013.01); *A61B 5/748* (2013.01); *G06K 9/00906* (2013.01); *G06K 9/46* (2013.01); *G06K 9/4652* (2013.01); *G06T 5/002* (2013.01); *G06T 7/0012* (2013.01); *G06T 7/0016* (2013.01); *G06T 7/90* (2017.01); *A61B 2560/0475* (2013.01); *G06T 2207/10016* (2013.01); *G06T 2207/30048* (2013.01)

(56) References Cited

U.S. PATENT DOCUMENTS

| | | | | |
|---|---|---|---|---|
| 8,562,526 | B2* | 10/2013 | Heneghan | A61B 5/0507 128/920 |
| 9,125,606 | B2* | 9/2015 | Verkruijsse | A61B 5/14552 |
| 2011/0158489 | A1 | 6/2011 | Huang et al. | |
| 2011/0251493 | A1 | 10/2011 | Poh et al. | |
| 2011/0311143 | A1 | 12/2011 | Cennini et al. | |
| 2013/0077823 | A1 | 3/2013 | Mestha et al. | |
| 2014/0275880 | A1* | 9/2014 | Verkruijsse | A61B 5/14552 600/323 |

FOREIGN PATENT DOCUMENTS

| | | |
|---|---|---|
| CN | 103083005 | 5/2013 |
| CN | 103729627 | 4/2014 |
| CN | 103761465 | 4/2014 |
| CN | 103793690 | 5/2014 |

OTHER PUBLICATIONS http://www.vitalsignscamera.com/; Jan. 14, 2016; pp. 1.
http://www.cardiio.com/; Jan. 14, 2016; pp. 1-3.
http://www.azumio.com/; Jan. 14, 2016; pp. 1-5.
https://play.google.com/store/apps/details?id=com.vitrox.facion.gui; Jan. 14, 2016; pp. 1-8.
Poh, M.Z., et al.; "Advancements in Non-Contact, Multiparameter Physiological Measurements Using a Webcam;" IEEE Transactions on Biomedical Engineering; vol. 58; No. 1; Jan. 2011; pp. 7-11.

* cited by examiner

LIVING BODY DETERMINATION DEVICES AND METHODS

CROSS REFERENCE TO RELATED APPLICATIONS

This application claims the benefit of U.S. Provisional Application No. 61/994,237, filed on May 16, 2014, and U.S. Provisional Application No. 62/134,110, filed on Mar. 17, 2015, the contents of which are incorporated herein by reference.

TECHNICAL FIELD

The invention relates to a determination device, and, more particularly, to a determination device for determining whether a subject is a living body according to a vital sign signal.

BACKGROUND

Recently, measurement apparatuses equipped with video cameras are provided to detect vital signs of human subjects (such as heart rate) through non-contact methods. There are several advantages of extracting vital signs by video camera; it is convenient, comfortable, and safe to the human subjects, because of the wireless and non-contact operation of the video cameras. Moreover, compared with major medical equipment, the cost of a video camera is low. For long-term monitoring in home care, the lower cost is beneficial to the user.

When user accidentally takes a measurement apparatus equipped with a video camera to capture frames of a non-living body, such as a picture, a statue, or a doll with human shape, the measurement apparatus performs vital-sign measurement operation as usual according to information contained in the captured frames. However, since the non-living body does not have any vital signs, the measurement result may be a random value or a measurement error occurs, which degrades usage experience.

SUMMARY

Thus, it is desirable to provide a determination device which can determine whether a subject is living body.

An exemplary embodiment of a determining device is provided. The determination device determines whether a subject shown in a plurality of frames captured by an image sensor has a vital-sign feature. The determination device comprises a detection module, a generation module, an evaluation module, and a determination module. The detection module detects a region of interest (ROI) on the subject. The generation module receives a plurality of sensing signals related to the ROI and generates a vital-sign signal. The evaluation module receives the vital-sign signal and evaluates a quality index of the vital-sign signal. The determination module determines whether the vital-sign signal is valid according to the quality index to determine whether the subject has the vital-sign feature.

An exemplary embodiment of a measurement apparatus for measuring a heart rate of a subject is provided. The measurement apparatus comprises an image sensor, a processor, and a heart-rate measurement device. The image sensor captures a plurality of frames to generate a plurality of sensing signals. A subject is shown in the plurality of frames. The processor detects a region of interest (ROI) on the subject, generates a vital-sign signal according to the sensing signals related to the ROI, evaluates a quality index of the vital-sign signal, and determines whether the subject is a living body according to the quality index to generate a determination signal. The heart-rate measurement device receives the determination signal and operates according to the determination signal.

An exemplary embodiment of a measurement method is provided. The measurement method comprises the steps of capturing a plurality of frames, wherein a subject is shown in the plurality of frames; detecting a region of interest (ROI) on the subject; generating a vital-sign signal according to the sensing signals related to the ROI; evaluating a quality index of the vital-sign signal; and determining whether the subject is a living body according to the quality index. A determination result of determining whether the subject is the living body is used to control a heart-rate measurement operation.

A detailed description is given in the following embodiments with reference to the accompanying drawings.

BRIEF DESCRIPTION OF DRAWINGS

The invention can be more fully understood by reading the subsequent detailed description and examples with references made to the accompanying drawings, wherein.

DETAILED DESCRIPTION

The following description is of the best-contemplated mode of carrying out the invention. This description is made for the purpose of illustrating the general principles of the invention and should not be taken in a limiting sense. The scope of the invention is best determined by reference to the appended claims.

Figure 1:
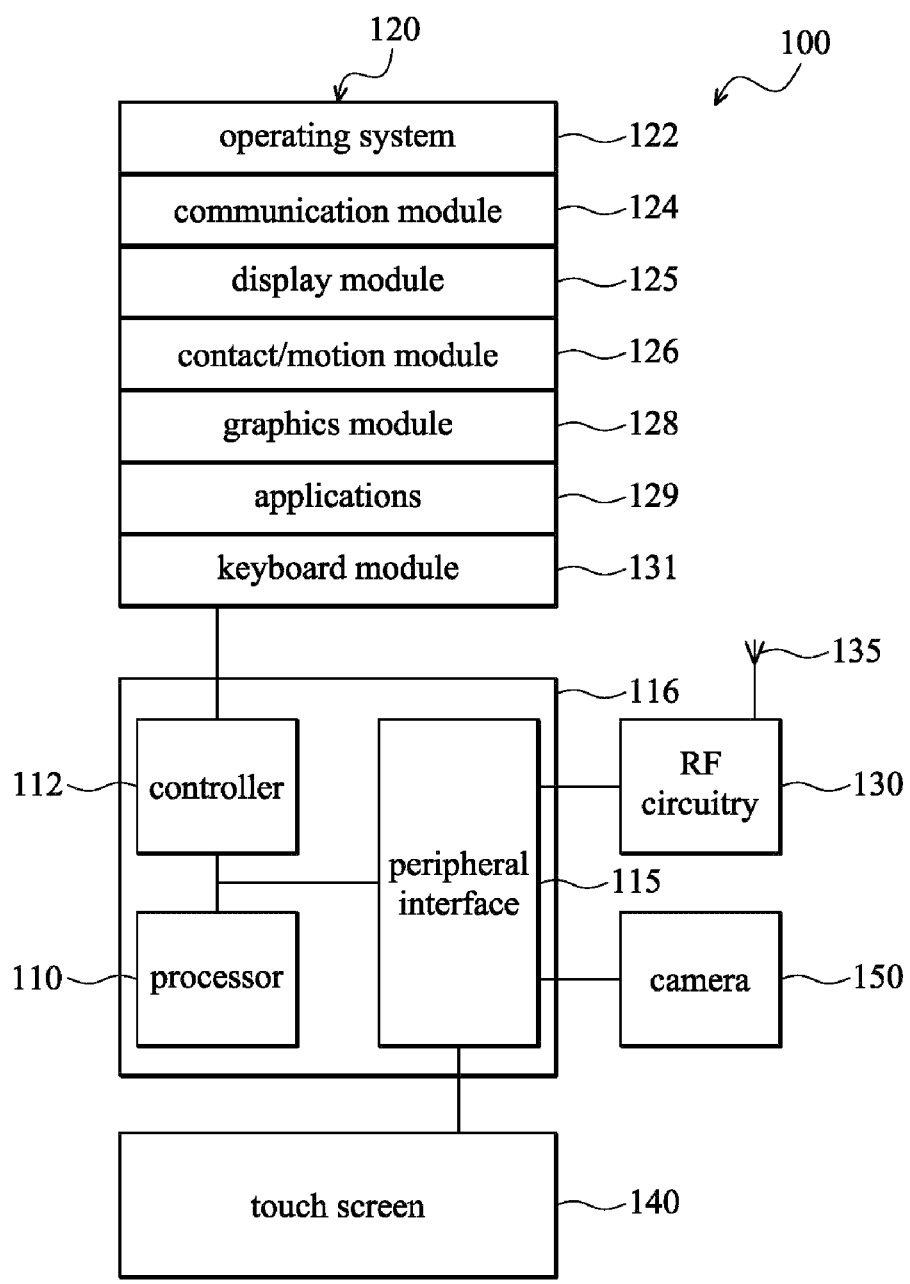
FIG. 1 is a schematic diagram illustrating a portable electronic device according to an exemplary embodiment of the invention.

FIG. 1 is a schematic diagram illustrating a portable electronic device 100 according to an exemplary embodiment of the invention. The portable electronic device 100 may comprise a processor 110, a memory unit 120, a RF circuitry 130 and a touch screen 140, and a camera 150. In an exemplary embodiment, the portable electronic device 100 may be a cellular telephone, a smartphone or a tablet PC. The processor 110 may be one or more data processors, digital signal processors, graphic processor, image processors and/or central processors, which are capable of executing one or more types of computer readable medium stored in the memory unit 120. The processor 110 is coupled to the RF circuitry 130, the touch screen 140, and the camera 150 through a peripheral interface 115, as illustrated in FIG. 1.

The RF circuitry 130 may be coupled to one or more antennas 135 and may allow communication with one or more additional devices, computers and/or servers using a wireless network. The portable electronic device 100 may support various communications protocols, such as code division multiple access (CDMA), Global System for Mobile Communications (GSM), Enhanced Data GSM Environment (EDGE), High-Speed Downlink Packet Access (HSDPA), Wi-Fi (such as IEEE 802.11a/b/g/n), Bluetooth, Wi-MAX, a protocol for email, instant messaging (IM), and/or a short message service (SMS), but the invention is not limited thereto.

The camera 150 may capture a plurality of frames from scenes and transmit signals related to the captured frames to the processor 110 through the peripheral interface 115. The peripheral interface 115 is coupled to the camera 150 by a wired or wireless connection manner. In the embodiment of FIG. 1, the camera 150 is equipped in the portable electronic device 100. However, in another embodiment, the camera 150 is implemented independently or implemented in another device and coupled to the portable electronic device 100 by a wired or wireless manner.

The touch screen 140 may detect contact and any movement or break thereof using any of a plurality of touch sensitivity technologies now known or to be later developed, including, but not limited to, capacitive, resistive, infrared, and surface acoustic wave technologies, as well as other proximity sensor arrays or other elements for determining one or more points of contact with the touch screen 140. However, the touch screen 140 may also display visual output from the portable electronic device 100. In some embodiments, the portable electronic device 100 may include circuitry (not shown in FIG. 1) for supporting a location determining capability, such as that provided by the Global Positioning System (GPS). In some embodiments, the touch screen 140 can be replaced by a display screen when the touch-sensitive function is not needed.

The memory controller 112 may be coupled to the memory unit 120, which may include one or more types of computer readable medium. The memory unit 120 may include high-speed random access memory (e.g. SRAM or DRAM) and/or non-volatile memory, such as one or more magnetic disk storage devices, one or more optical storage devices, and/or flash memory. The memory unit 120 may store an operating system 122, such as LINUX, UNIX, OS X, WINDOWS, Android, or an embedded operating system such as VxWorks. The operating system 122 may include procedures for handling basic system services and for performing hardware dependent tasks. The memory unit 120 may also store communication procedures in a communication module 124. The communication procedures may be used for communicating with one or more additional devices, one or more computers and/or one or more servers. The memory unit 120 may include a display module 125, a contact/motion module 126 to determine one or more points of contact and/or their movement, and a graphics module 128. The graphics module 128 may support widgets, that is, modules or applications with embedded graphics. The widgets may be implemented using JavaScript, HTML, Adobe Flash, or other suitable computer program languages and technologies.

The memory unit 120 may also include one or more applications 129. For example, applications stored in the memory unit 120 may include telephone applications, email applications, text messaging or instant messaging applications, memo pad applications, address books or contact lists, calendars, picture taking and management applications, and music playing and management applications. The applications 129 may include a web browser (not shown in FIG. 1) for rendering pages written in the Hypertext Markup Language (HTML), Wireless Markup Language (WML), or other languages suitable for composing web pages or other online content. The memory unit 120 may further include a keyboard module (or a set of instructions) 131. The keyboard module 131 operates one or more soft keyboards.

It should be noted that each of the above identified modules and applications correspond to a set of instructions for performing one or more functions described above. These modules (i.e., sets of instructions) need not be implemented as separate software programs, procedures or modules. The various modules and sub-modules may be rearranged and/or combined. Various functions of the portable electronic device 100 may be implemented in hardware and/or in software, including in one or more signal processing and/or application specific integrated circuits.

Figure 2:
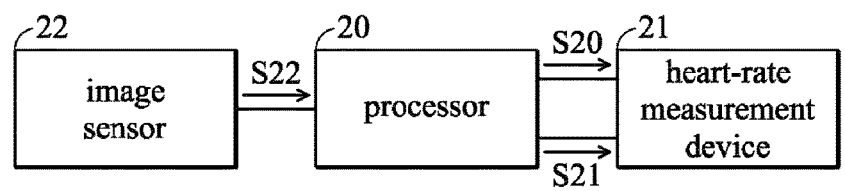
FIG. 2 shows one exemplary embodiment of an electronic system.

FIG. 2 shows an exemplary embodiment of an electronic system. As shown in FIG. 2, an electronic system 2 comprises a processor 20, a heart-rate measurement device 21, and an image sensor 22. The processor 20 operates to determine whether a subject is a living body. The image sensor 22 operates to capture a plurality of successive frames from scenes where a subject exists. Thus, the subject is shown in the captured frame. In each frame, the image sensor 22 generates a plurality of sensing signals S22 respectively derived from a plurality of pixels of a sensing array of the image sensor 22. The processor 20 is coupled to the image sensor 22 to receive sensing signals S22 related to the captured frames. The processor 20 detects a region of interest (ROI) on the subject. Since the color of the skin of a living body can change when blood flows through it due to the systole and diastole of the heart, the face area of the living body is a proper area for determining whether the subject is a living body. In one embodiment, the processor 20 performs a face detection operation to search the face area of the subject to serve as the ROI. In another embodiment, to obtain an accurate determination result, the processor 20 performs a face detection operation to search a face area of the subject and further performs a skin segmentation operation to search a skin region in the face area. Accordingly, the skin region in the area serves as the ROI.

In some embodiments, since the subject may move, the ROI will move with the movement of the subject. Thus, in the captured frames, the processor 20 is capable of performing a tracking operation to track the ROI. For example, the processor 20 performs at least one tracking algorithm to track the ROI, such as an algorithm comprising at least one of mean shift, particle filter, or mosses.

When the ROI is detected, the processor 20 generates a vital-sign signal S21 according to the sensing signals S22 related to the ROI. As described above, in a case that a living body is captured by a camera with a sensing array in successive frames, since the color of the skin of the living body can change when blood flows through it due to the systole and diastole of the heart, the color information of the pixels of the sensing array corresponding to the skin can be used to generate a vital-sign signal related to the heart-rate of the living body. The color information may be RGB, YUV, YcrCb, grayscale, infrared data, or sensor raw, In the embodiment, the processor 20 calculates an average value of at least one color component (such as R, G, and/or B component) of the pixels, involved in the sensing signals S22 related to the ROI, within the time-interval of the captured frames, to generate an average signal. The processor 20 then generates a vital-sign signal S21 according to the average signal. Since the vital-sign signal S21 is generated according to the average signal which is related to the change of the color of the skin in the ROI, the vital-sign signal S21 can be used to estimate the heart rate of the subject. In an embodiment, the average signal directly serves as the vital-sign signal S21.

In another embodiment, in order to enhance the accuracy of the determination performed by the processor 20, the processor 20 may perform a filtering operation on the average signal to generate the vital-sign signal S21 to filter noise or components of the average signal which are out of the range of the frequencies related to a heart rate of a living body. In general, a frequency of a signal generated according a heart rate of a human being is in a range of 50-200 BPM (Beats per Minute). Thus, the components of the signal which are out of the range of 50-200 BPM are useless to estimate the heat rate. In the embodiment, the processor 20 may perform the filtering operation to filter the components which are out of the range of 50-200 BPM. In further another embodiment, the processor 20 may not only perform the above filter operation on the average signal but also perform an independent component analysis on the average to generate the vital-sign signal S21.

Figure 3:
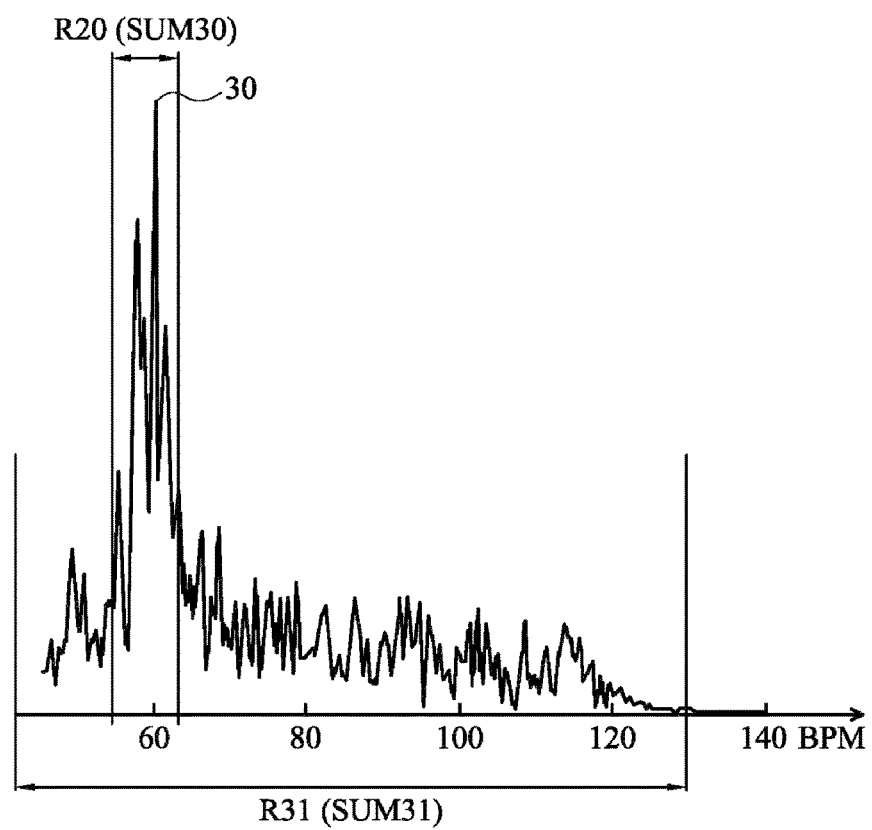
FIG. 3 is a schematic diagram illustrating evaluation of a quality index of a vital-sign signal according to one exemplary embodiment.

Then, the processor 20 transforms the vital-sign signal S21 from the time domain to a frequency domain. The processor 20 detects a peak value of energy of the vital-sign signal S21 in the frequency domain. FIG. 3 shows the vital-sign signal S21 without suffering the filtering operation and the independent component analysis. As shown in FIG. 3, a peak value 30 of the energy is detected, and the peak value 30 corresponds to about frequency value 60 BPM. The processor 20 defines a frequency range R30 which contains 60 BPM, such as a frequency range from 55 BPM to 62 BPM. The processor 20 further defines a frequency range R31 which contains the frequency range R30, such as a frequency range from 40 BPM to 110 BPM. The processor 20 calculates the sum SUM30 of the energy of the vital-sign signal S21 in the frequency range R30 and the sum SUM31 of the energy of the vital-sign signal S21 in the frequency range R30. Then, the processor 20 calculates the ratio (frequency ratio) of the sum SUM30 and the SUM31 (SUM30/SUM31) for evaluating a quality index.

Figure 4:
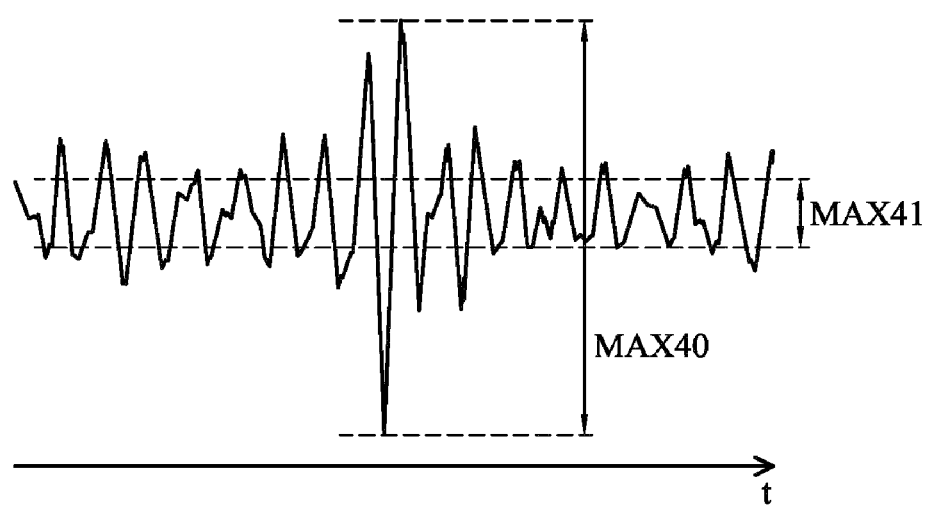
FIG. 4 is a schematic diagram illustrating evaluation of a quality index of a vital-sign signal according to another exemplary embodiment.

In another embodiment, as shown in FIG. 4, the processor 20 may detect the maximum amplitude MAX40 of the vital-sign signal S21 in the time domain and further calculate the average amplitude MAX41 of the vital-signal signal S21. The processor 20 calculates the ratio (amplitude ratio) of the maximum amplitude MAX40 and the average amplitude MAX41. In this embodiment, the processor 20 evaluates the quality index according to both of the frequency ratio and the amplitude ratio.

The processor 20 then determines whether the vital-sign signal S21 is valid according to the quality index and generates a determination signal S20 according to the determination result. In the case that only the frequency ratio is used for evaluating the quality index, the processor 20 compares the frequency ratio with a predetermined frequency ratio. When the frequency ratio is greater than the predetermined frequency ratio, the processor 20 determines that the vital-sign signal S21 is valid. The valid vital-sign signal S21 indicates that a heart rate which is in a normal range for living bodies is obtained from the ROI, that is the subject has the vital-sign feature. Accordingly, the processor 20 determines that the subject is a living body. When the frequency ratio is less than the predetermined frequency ratio, the processor 20 determines that the vital-sign signal S21 is not valid, which indicates that the subject does not have the vital-sign feature. Accordingly, the processor 20 determines that the subject is not a living body.

In the case that both of the frequency ratio and the amplitude ratio are used for evaluating the quality index, the processor 20 performs the above comparison operation on the frequency ratio. The processor 20 further compares the amplitude ratio with a predetermined amplitude ration. The amplitude ratio greater than the predetermined amplitude ration indicates that the subject moves by great shifting in the time-interval of the captured frames, which result in worse quality of the vital-sign signal S21. The amplitude ratio less than the predetermined amplitude ration indicates that the subject does not move or move by slight shifting by great shifting in the time-interval of the captured frames, which result in better quality of the vital-sign signal S21. When the frequency ratio is greater than the predetermined frequency ratio and the amplitude ratio is less than the predetermined amplitude ration, the processor 20 determines that the vital-sign signal S21 is valid. When the frequency ratio is less than the predetermined frequency ratio and/or the amplitude ratio is greater than the predetermined amplitude ration, the processor 20 determines that the vital-sign signal S21 is not valid.

In some embodiments, the processor 20 may perform living-body detection by detecting facial expression and/or eye blinking of the subject. The processor 20 determines whether the vital-sign signal S21 is valid according to the quality index and the result of the living-body detection.

According to the above description, the processor 20 is capable of determining whether a subject is a living body according to the vital-sign signal S21 derived from an ROI on the subject. The determination signal S20 generated by the processor 20 may be used to control the operation of the heart-rate measurement rate.

Figure 5:
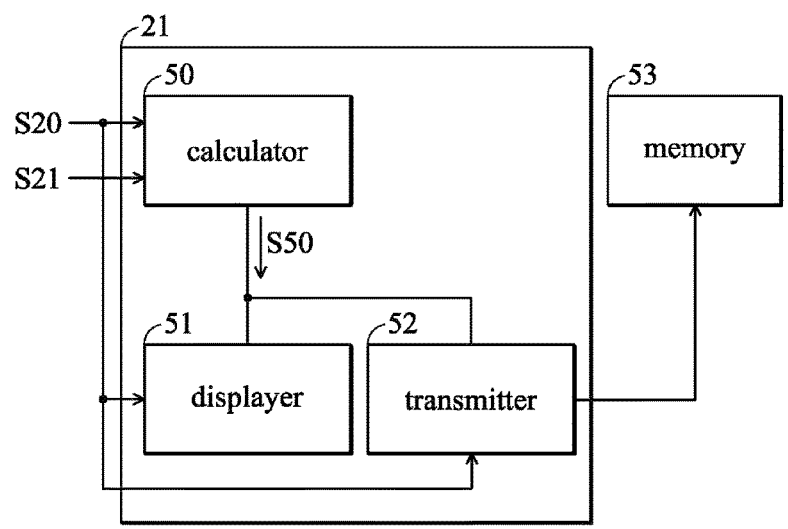
FIG. 5 shows an exemplary embodiment of a heart rate measurement device.

In an embodiment, as shown in FIG. 5, the heart-rate measurement device 21 comprises a calculator 50 and a displayer 51. The calculator 50 receives the vital-sign signal S21 and performs a heart-rate calculation operation on the vital-sign signal S21 to obtain a heart-rate value S50 according to the vital-sign signal S21. The displayer 51 is coupled to the calculator 50 to receive the heart-rate value S50 and controlled by the determination signal. When the processor 20 determines that the vital-sign signal is valid (that is the subject is a living body), the displayer 51 is controlled by the determination signal S21 to show the heart-rate value S50. When the processor 20 determines that the vital-sign signal S21 is not valid (that is the subject is not a living body), the displayer 51 is controlled by the determination signal S21 and does not show the heart-rate value S50.

In another embodiment, the calculator 50 may further receive the determination signal S21. The calculator 50 is controlled by the determination signal S21 to perform a heart-rate statistics operation. When the processor determines that the vital-sign signal is valid (that is the subject is a living body), the calculator 50 is controlled by the determination signal S21 to apply the heart-rate value in the heart-rate statistics operation. When the processor 20 determines that the vital-sign signal S21 is not valid (that is the subject is not a living body), the calculator 50 is controlled by the determination signal S21 to omit applying the heart-rate value in the heart-rate statistics operation.

The heart-rate measurement device 21 may further comprise a transmitter 52. The transmitter is coupled to the calculator 50 to receive the hear-rate value S50 and controlled by the determination signal S20. When the processor determines that the vital-sign signal is valid (that is the subject is a living body), the transmitter 52 is controlled by the determination signal S20 to transmit the heart-rate value S50 to a memory 53 for storage. In the embodiment, the memory 53 is equipped in the electronic system 2 or implemented by a storage which connects the transmitter 52 through wireless communication, such as a cloud storage.

In further another embodiment, the calculator 50 may not always perform heart-rate calculation operation each time when the vital-sign signal is received. Whether the heart-rate calculation operation is performed may be determined according to the determination signal S20. When the processor 20 determines that the vital-sign signal is valid (that is the subject is a living body), the calculator 50 is controlled by the determination signal S20 to perform the heart-rate calculation operation on the vital-sign signal S21 to obtain the heart-rate value S50. When the processor 20 determines that the vital-sign signal S21 is not valid (that is the subject is not a living body), the calculator 50 is controlled by the determination signal S20 not to perform the heart-rate calculation operation on the vital-sign signal S21.

In the embodiment of FIG. 2, the electronic system 2 may be implemented by a measurement apparatus, such as the portable electronic device 100 shown in FIG. 1. In this case, the processor 20 may be implemented by the processor 110 of FIG. 1, and the image sensor 22 may be a camera, such as the camera 150 shown in FIG. 1. The heart-rate measurement device 21 may be implemented by different portions in the portable electronic device 100, such as the processor 110 for calculating the heart-rate value S50, the touch screen 140 for displaying the heart-rate value S50, and the RF circuitry 130 for transmitting the heart-rate value S50.

According to the above embodiment, when the subject is not a living body, the calculated heart-rate value may be not displayed or may be omitted, thereby enhancing the usage experience.

Figure 6:
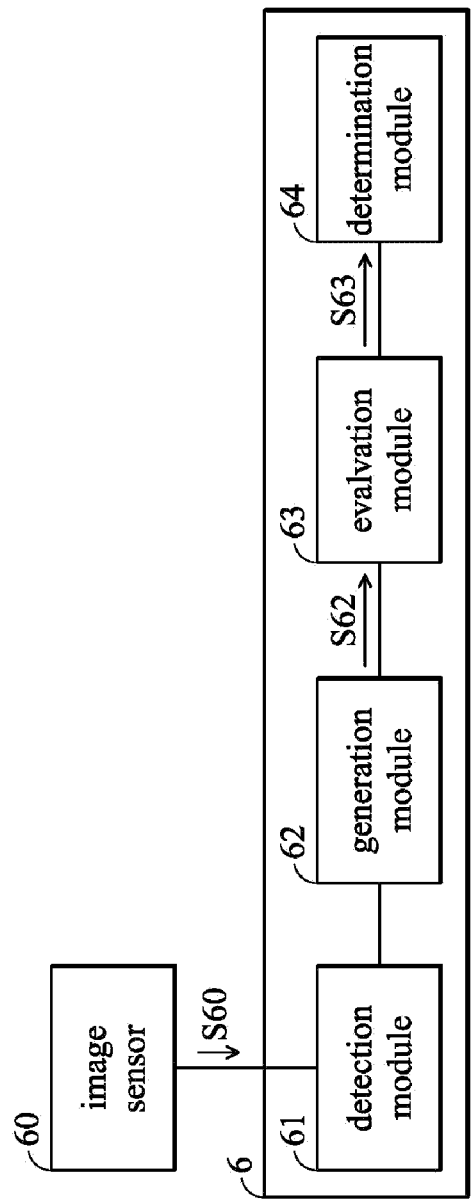
FIGS. 6 and 7 show exemplary embodiments of a determination device.

FIG. 6 shows an exemplary embodiment of a determination device. As shown in FIG. 6, a determination device 6 comprises a detection module 61, a generation module 62, an evaluation module 63, and a determination module 64. The determination device 6 operates to determine whether a subject is a living body. There is an image sensor 60 coupled to the determination device 6 by a wired or wireless connection manner. The image sensor 60 operates to capture a plurality of successive frames from scenes where a subject exists. Thus, the subject is shown in the captured frames. In each frame, the image sensor 60 generates a plurality of sensing signals S60 respectively derived from a plurality of pixels of a sensing array of the image sensor 60. The detection module 61 is coupled to the image sensor 60 to receive sensing signals S60 related to the captured frames. The detection module 61 detects a region of interest (ROI) on the subject. Since the color of the skin of a living body can change when blood flows through it due to the systole and diastole of the heart, the face area of the living body is a proper area for determining whether the subject is a living body. In one embodiment, the detection module 61 performs a face detection operation to search the face area of the subject to serve as the ROI. In another embodiment, to obtain an accurate determination result, the detection module 61 performs a face detection operation to search a face area of the subject and further performs a skin segmentation operation to search a skin region in the face area. Accordingly, the skin region in the area serves as the ROI. In the embodiment, the ROI covers a plurality of pixels of a sensing array of the image sensor 22 in each frame, and one sensing signal S22 is generated from one pixel.

In some embodiments, since the subject may move, the ROI will move with the movement of the subject. Thus, in the captured frames, the detection module 61 is capable of performing a tracking operation to track the ROI. For example, the processor 20 performs at least one tracking algorithm to track the ROI, such as an algorithm comprising at least one of mean shift, particle filter, or mosses.

When the ROI is detected, the generation module 62 generates a vital-sign signal S62 according to the sensing signals S60 related to the ROI. As described above, in a case that a living body is captured by a camera with a sensing array in successive frames, since the color of the skin of the living body can change when blood flows through it due to the systole and diastole of the heart, the color information of the pixels of the sensing array corresponding to the skin can be used to generate a vital-sign signal related to the heart-rate of the living body. The color information may be RGB, YUV, YcrCb, grayscale, infrared data, or sensor raw, In the embodiment, the generation module 62 calculates an average value of at least one color component (such as R, G, and/or B component) of the pixels, involved in the sensing signals S60 related to the ROI, within the time-interval of the captured frames, to generate an average signal. The generation module 62 then generates a vital-sign signal S62 according to the average signal. Since the vital-sign signal S62 is generated according to the average signal which is related to the change of the color of the skin in the ROI, the vital-sign signal S62 can be used to estimate the heart rate of the subject. In an embodiment, the average signal directly serves as the vital-sign signal S62.

In another embodiment, in order to enhance the accuracy of the determination performed by the determination device 6, the generation module 62 may perform a filtering operation on the average signal to generate the vital-sign signal S62 to filter noise or components of the average signal which are out of the range of the frequencies related to a heart rate of a living body. In general, a frequency of a signal generated according a heart rate of a human being is in a range of 50-200 BPM. Thus, the components of the signal which are out of the range of 50-200 BPM are useless to estimate the heat rate. In the embodiment, the generation module 62 may perform the filtering operation to filter the components which are out of the range of 50-200 BPM. In further another embodiment, the generation module 62 may not only perform the above filter operation on the average signal but also perform an independent component analysis on the average to generate the vital-sign signal S62.

Then, the evaluation module 63 transforms the vital-sign signal S62 from the time domain to a frequency domain. The evaluation module 63 detects a peak value of energy of the vital-sign signal S62 in the frequency domain. FIG. 3 shows the vital-sign signal S62 without suffering the filtering operation and the independent component analysis. As shown in FIG. 3, a peak value 30 of the energy is detected, and the peak value 30 corresponds to about frequency value 60 BPM. The evaluation module 63 defines a frequency range R30 which contains 60 BPM, such as a frequency range from 55 BPM to 62 BPM. The evaluation module 63 further defines a frequency range R31 which contains the frequency range R30, such as a frequency range from 40 BPM to 110 BPM. The evaluation module 63 calculates the sum SUM30 of the energy of the vital-sign signal S62 in the frequency range R30 and the sum SUM31 of the energy of the vital-sign signal S62 in the frequency range R30. Then, the evaluation module 63 calculates the ratio (frequency ratio) of the sum SUM30 and the SUM31 (SUM30/SUM31) for evaluating a quality index S63.

In another embodiment, as shown in FIG. 4, the evaluation module 63 may detect the maximum amplitude MAX40 of the vital-sign signal S62 in the time domain and further calculate the average amplitude MAX41 of the vital-signal signal S62. The evaluation module 63 calculates the ratio (amplitude ratio) of the maximum amplitude MAX40 and the average amplitude MAX41. In this embodiment, the evaluation module 63 evaluates the quality index S63 according to both of the frequency ratio and the amplitude ratio.

After the determination module 64 receives the quality index S63 the determination module 64 then determines whether the vital-sign signal S62 is valid according to the quality index according to the determination result. In the case that only the frequency ratio is used for evaluating the quality index, the determination module 64 compares the frequency ratio with a predetermined frequency ratio. When the frequency ratio is greater than the predetermined frequency ratio, the determination module 64 determines that the vital-sign signal S62 is valid. The valid vital-sign signal S62 indicates that a heart rate which is in a normal range for living bodies is obtained from the ROI, that is the subject has the vital-sign feature. Accordingly, the determination module 64 determines that the subject is a living body. When the frequency ratio is less than the predetermined frequency ratio, the determination module 64 determines that the vital-sign signal S62 is not valid, which indicates that the subject does not have the vital-sign feature. Accordingly, the determination module 64 determines that the subject is not a living body.

In the case that both of the frequency ratio and the amplitude ratio are used for evaluating the quality index, the determination module 64 performs the above comparison operation on the frequency ratio. The determination module 64 further compares the amplitude ratio with a predetermined amplitude ration. The amplitude ratio greater than the predetermined amplitude ration indicates that the subject moves by great shifting in the time-interval of the captured frames, which result in worse quality of the vital-sign signal S62. The amplitude ratio less than the predetermined amplitude ration indicates that the subject does not move or move by slight shifting by great shifting in the time-interval of the captured frames, which result in better quality of the vital-sign signal S62. When the frequency ratio is greater than the predetermined frequency ratio and the amplitude ratio is less than the predetermined amplitude ration, the determination module 64 determines that the vital-sign signal S62 is valid. When the frequency ratio is less than the predetermined frequency ratio and/or the amplitude ratio is greater than the predetermined amplitude ration, the determination module 64 determines that the vital-sign signal S62 is not valid.

In some embodiments, the determination module 64 may further perform living-body detection by detecting facial expression and/or eye blinking. The determination module 64 then determines whether the vital-sign signal S61 is valid according to the quality index and the result of the living-body detection.

According to the above description, the determination device 6 is capable of determining whether a subject is a living body according to the vital-sign signal S62 derived from an ROI on the subject. The determination result may be used to a measurement device, which is coupled to the determination device 6, for measurement vital-signs, such as heart rate.

Figure 7:
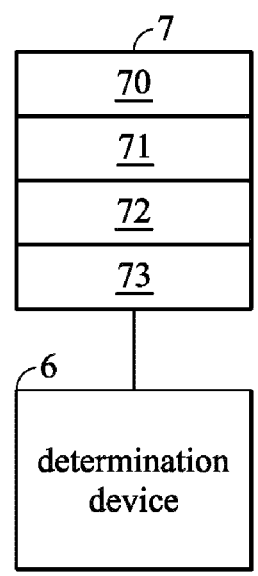

In the embodiment of FIG. 6, the detection device 6 may be implemented by a processor, such as the processor 110 shown in FIG. 1. In an embodiment, each of the modules in the determination device 6 may be implemented in a processor, such as the processor 1 shown in FIG. 1 by hardware and/or software performing one or more corresponding functions described above. In another embodiment, a memory is coupled to the determination device 6. As shown in FIG. 7, a memory 7 stores sets of instructions (or coding) 70, 71, 72, and 73, respectively corresponding to the functions of the modules of FIG. 6. The determination device 6 is coupled to the memory 7 to load the sets of instructions 70-73. When the determination device 6 performs any one set of instructions, the hardware and/or software in the determination device 6 is referred to as the corresponding module. For example, when the determination device 6 performs the set of instructions related to the quality-index evaluation function, the hardware and/or software in the determination device 6 is referred to as the evaluation module 63.

Figure 8:
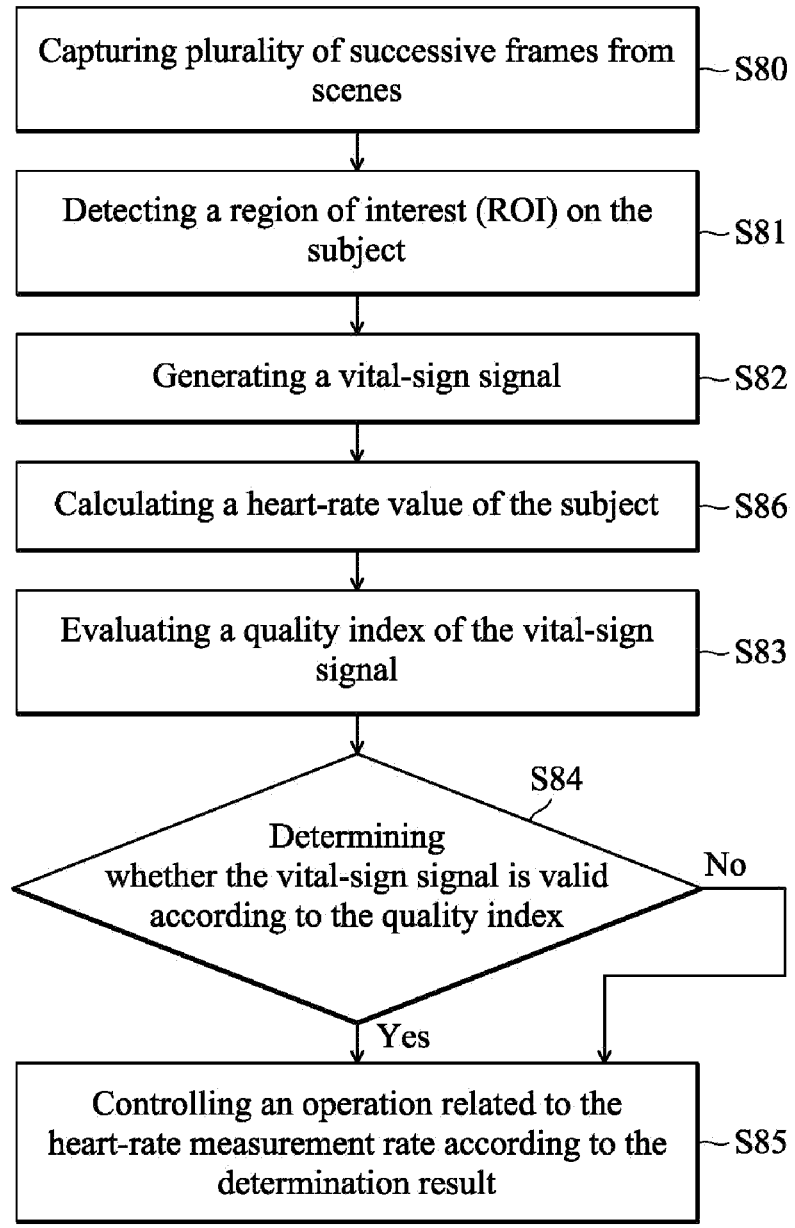
FIGS. 8-12 show exemplary embodiments of a measurement method.

FIG. 8 shows one exemplary embodiment of a measurement method. The determination method may be performing by at least one processor, such as the portable electronic device 100 shown in FIG. 1 or the electronic system 2 shown in FIG. 2. The measurement method is performed to determine whether a subject is a living body and further to measure vital-sign of the subject. The measurement method comprises a step (S80) of capturing plurality of successive frames from scenes where a subject exists by an image sensor, such as the camera 150 shown in FIG. 1. Thus, the subject is shown in the captured frames. In each frame, a plurality of sensing signals are generated respectively from a plurality of pixels of a sensing array of the image sensor. The measurement method further comprising a step (S81) of detecting a region of interest (ROI) on the subject. Since the color of the skin of a living body can change when blood flows through it due to the systole and diastole of the heart, the face area of the living body is a proper area for determining whether the subject is a living body. In one embodiment, a face detection operation is performed in the step S81 to search the face area of the subject to serve as the ROI. In another embodiment, a face detection operation is performed in the step S81 to search a face area of the subject, and a skin segmentation operation id further performed in the step S81 to search a skin region in the face area. Accordingly, the skin region in the area serves as the ROI.

In some embodiments, since the subject may move, the ROI will move with the movement of the subject. Thus, in the captured frames, a tracking operation to track the ROI may be performed in the step S81. For example, at least one tracking algorithm to track the ROI, such as an algorithm comprising at least one of mean shift, particle filter, or mosses are performed for tracking the ROI.

The measurement method also comprises a step (S82) of generating a vital-sign signal according to the sensing signals related to the ROI. As described above, in a case that a living body is captured by a camera with a sensing array in successive frames, since the color of the skin of the living body can change when blood flows through it due to the systole and diastole of the heart, the color information of the pixels of the sensing array corresponding to the skin can be used to generate a vital-sign signal related to the heart-rate of the living body. The color information may be RGB, YUV, YcrCb, grayscale, infrared data, or sensor raw, In the embodiment, in the step S82 an average value of at least one color component (such as R, G, and/or B component) of the pixels, involved in the sensing signals S22 related to the ROI, within the time-interval of the captured frames, is calculated to generate an average signal. The vital-sign signal is generated according to the average signal. Since the vital-sign signal is generated according to the average signal which is related to the change of the color of the skin in the ROI, the vital-sign signal can be used to estimate the heart rate of the subject. In an embodiment, the average signal directly serves as the vital-sign signal.

In another embodiment, in order to enhance the accuracy of the determination and the measurement, in the step S82, a filtering operation is performed on the average signal to generate the vital-sign signal to filter noise or components of the average signal which are out of the range of the frequencies related to a heart rate of a living body. In general, a frequency of a signal generated according a heart rate of a human being is in a range of 50-200 BPM. Thus, the components of the signal which are out of the range of 50-200 BPM are useless to estimate the heat rate. In the embodiment, the filtering operation is performed to filter the components which are out of the range of 50-200 BPM. In further another embodiment, not only the above filter operation but also an independent component analysis is performed on the average to generate the vital-sign signal.

The measurement method comprises a step (S83) of evaluating a quality index of the vital-sign signal. In the step S83, the vital-sign signal is transformed from the time domain to a frequency domain. A peak value of energy of the vital-sign signal in the frequency domain is detected. FIG. 3 shows the vital-sign signal without suffering the filtering operation and the independent component analysis. As shown in FIG. 3, a peak value 30 of the energy is detected, and the peak value 30 corresponds to about frequency value 60 BPM. A frequency range R30 which contains 60 BPM, such as a frequency range from 55 BPM to 62 BPM, is defined. A frequency range R31 which contains the frequency range R30, such as a frequency range from 40 BPM to 110 BPM, is also defined. The sum SUM30 of the energy of the vital-sign signal S21 in the frequency range R30 is calculated, and the sum SUM31 of the energy of the vital-sign signal S21 in the frequency range R30 is calculated. Then, the ratio (frequency ratio) of the sum SUM30 and the SUM31 (SUM30/SUM31) is calculated for evaluating a quality index.

In another embodiment, as shown in FIG. 4, in the step S83, the maximum amplitude MAX40 of the vital-sign signal in the time domain is detected, and the average amplitude MAX41 of the vital-signal signal is calculated the ratio (amplitude ratio) of the maximum amplitude MAX40 and the average amplitude MAX41 is calculated. In this embodiment, the quality index is evaluated according to both of the frequency ratio and the amplitude ratio.

The determination method is further comprises a step (S84) of determining whether the vital-sign signal is valid according to the quality index. In the case that only the frequency ratio is used for evaluating the quality index, the step S84 is performed by comparing the frequency ratio with a predetermined frequency ratio. When the frequency ratio is greater than the predetermined frequency ratio, it is determined that the vital-sign signal is valid. The valid vital-sign signal S21 indicates that a heart rate which is in a normal range for living bodies is obtained from the ROI, that is the subject has the vital-sign feature. Accordingly, it is determined that the subject is a living body. When the frequency ratio is less than the predetermined frequency ratio, it is determined that the vital-sign signal S21 is not valid, which indicates that the subject does not have the vital-sign feature. Accordingly, it is determined that the subject is not a living body.

In the case that both of the frequency ratio and the amplitude ratio are used for evaluating the quality index, the step S84 is performed by performing the above comparison operation on the frequency ratio and comparing the amplitude ratio with a predetermined amplitude ration. The amplitude ratio greater than the predetermined amplitude ration indicates that the subject moves by great shifting in the time-interval of the captured frames, which result in worse quality of the vital-sign signal. The amplitude ratio less than the predetermined amplitude ration indicates that the subject does not move or move by slight shifting by great shifting in the time-interval of the captured frames, which result in better quality of the vital-sign signal. When the frequency ratio is greater than the predetermined frequency ratio and the amplitude ratio is less than the predetermined amplitude ration, it is determined that the vital-sign signal is valid. When the frequency ratio is less than the predetermined frequency ratio and/or the amplitude ratio is greater than the predetermined amplitude ration, it is determined that the vital-sign signal is not valid.

In some embodiments, living-body detection may be performed by detecting facial expression and/or eye blinking. Thus, in the step S84, whether the vital-sign signal S61 is valid is determined according to the quality index and the result of the living-body detection.

According to the above description, the steps S80-S84 are performed to determine whether a subject is a living body according to the vital-sign signal derived from an ROI on the subject. The determination result may be used to control the operation related to the heart-rate measurement rate (step S85).

In the embodiment of FIG. 8 after the vital-sign signal is generated in the step S82, a step (S86) of calculating a heart-rate value of the subject is performed. In FIG. 8, the step S86 is performed between the steps S82 and S83. However, in other embodiments, the step S86 may be performed between the steps S83 and S84 or after the step S84.

Figure 9:
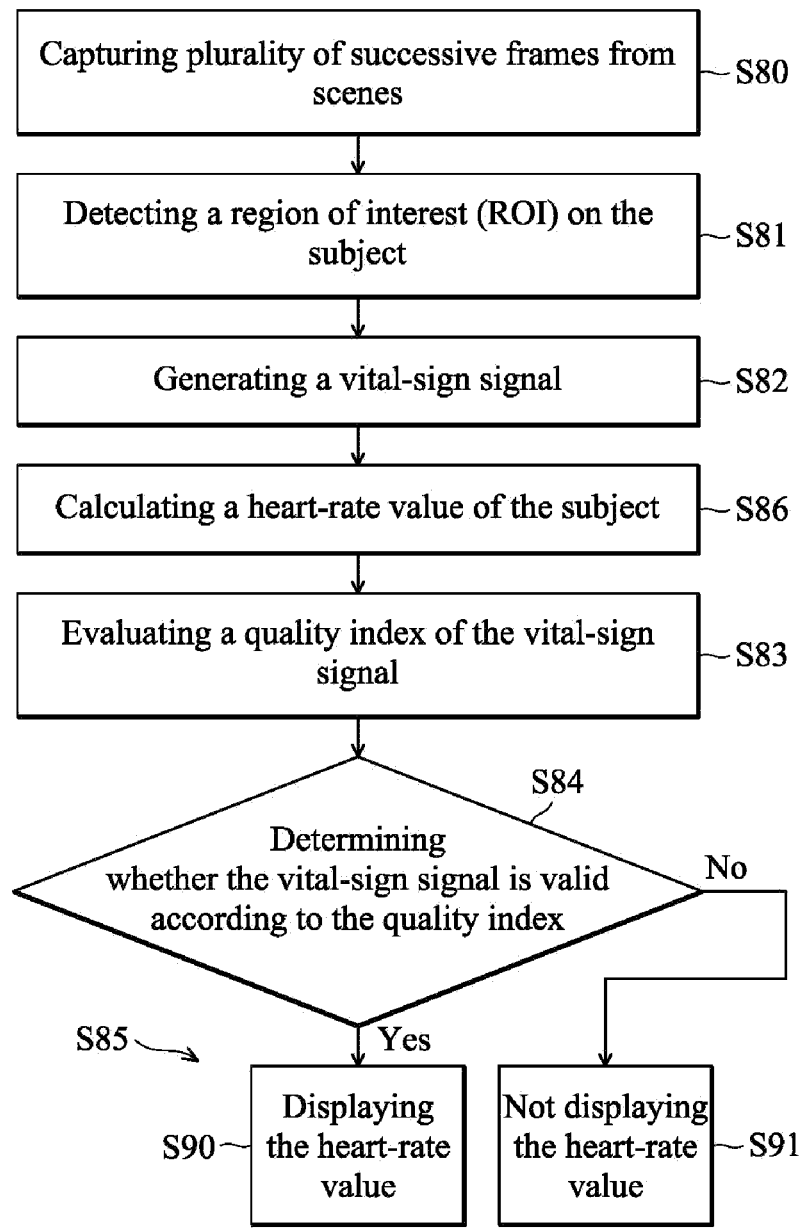

FIG. 9 shows one exemplary embodiment of the step of controlling the operation related to the heart-rate measurement rate. As shown in FIG. 9, in the step S85, when it is determined that the vital-sign signal is valid (that is the subject is a living body), the heart-rate value is displayed on a displayer (step S90). When it is determined that the vital-sign signal is not valid (that is the subject is not a living body), the vital-sign signal is not displayed on a displayer (step S91).

Figure 10:
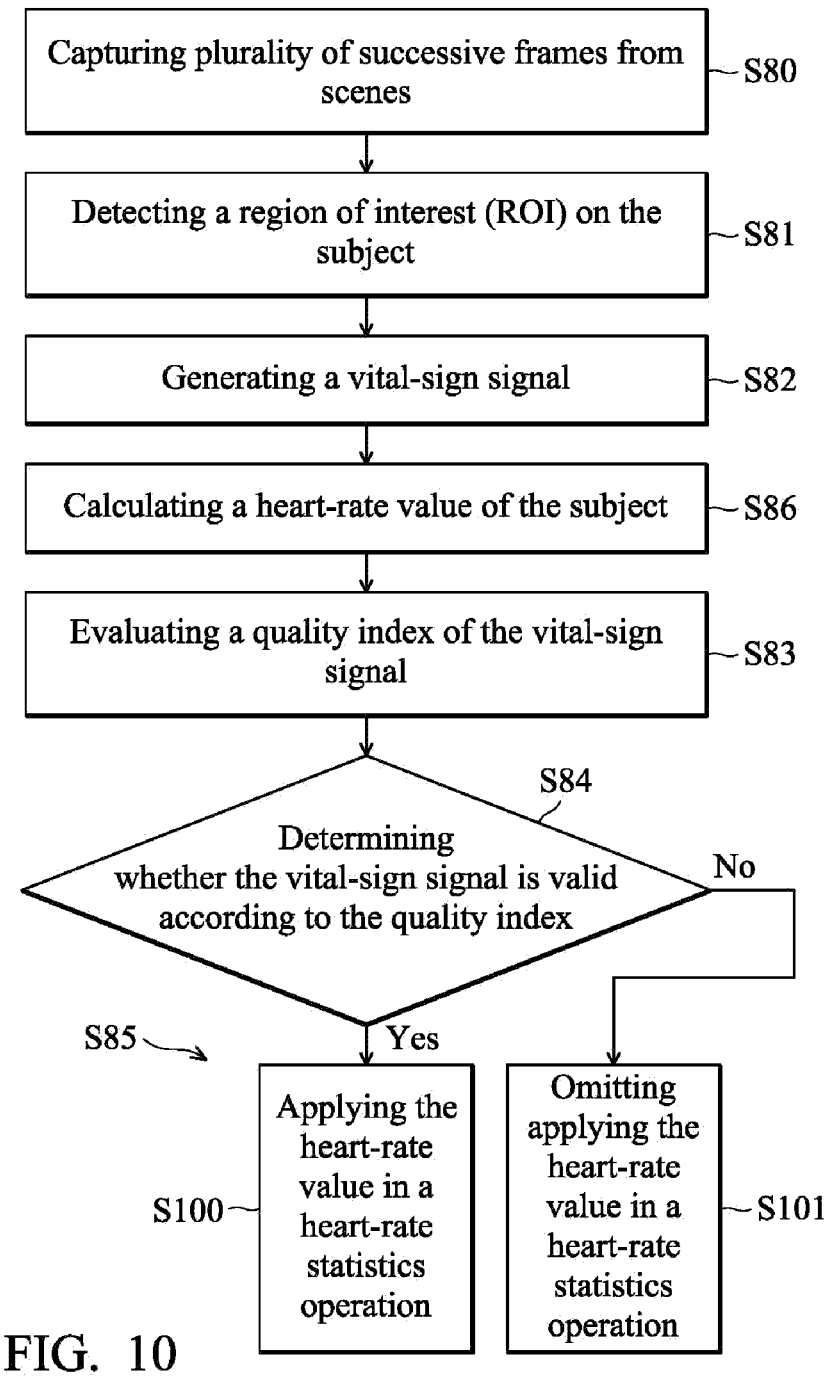

FIG. 10 shows another exemplary embodiment of the step of controlling the operation related to the heart-rate measurement rate. As shown in FIG. 10, in the step S85, when it is determined that the vital-sign signal is valid (that is the subject is a living body), the heart-rate value is applied in a heart-rate statistics operation (step S100). When it is determined that the vital-sign signal is not valid (that is the subject is not a living body), the heart-rate value is (step S101).

Figure 11:
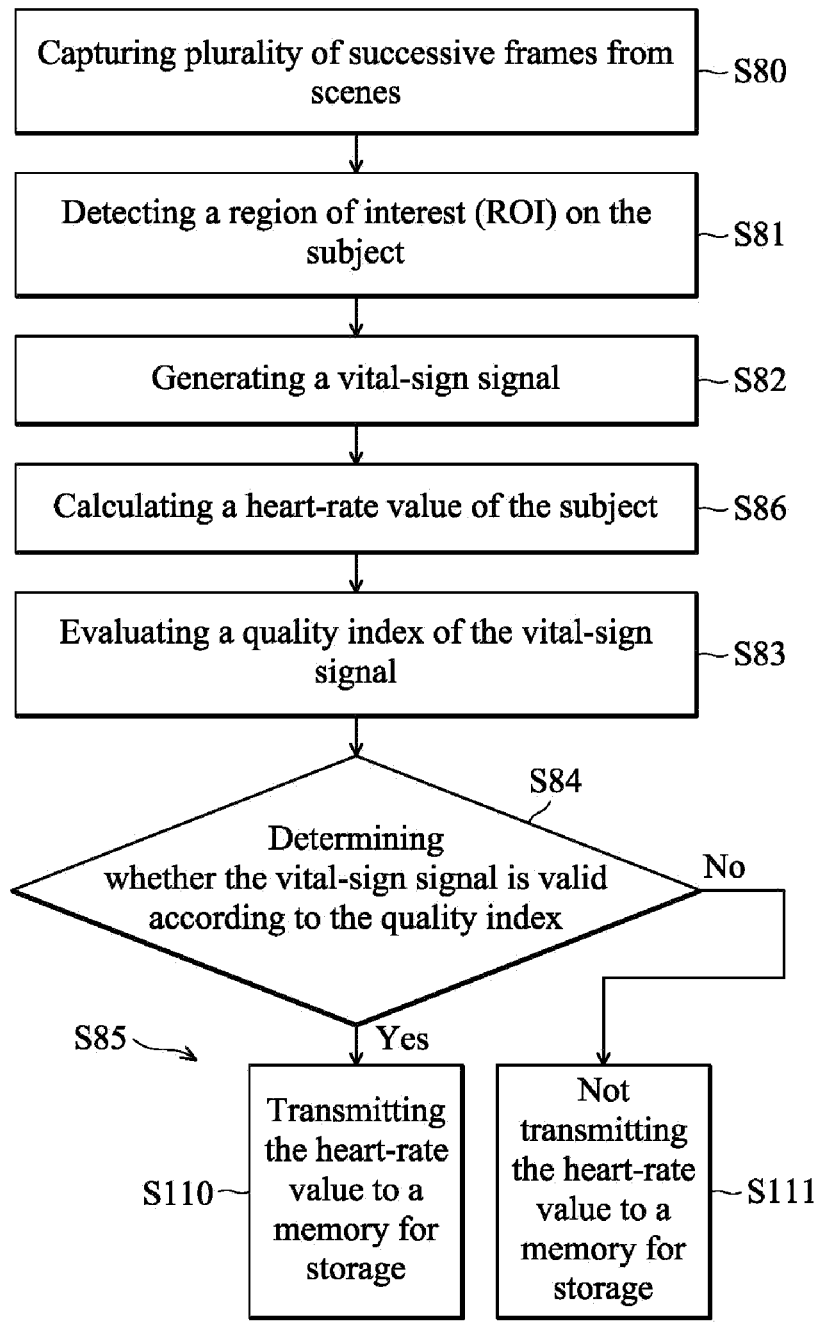

FIG. 11 shows further another exemplary embodiment of the step of controlling the operation related to the heart-rate measurement rate. As shown in FIG. 11, in the step S85, when it is determined that the vital-sign signal is valid (that is the subject is a living body), the heart-rate value is transmitted to a memory for storage (step S110). When it is determined that the vital-sign signal is not valid (that is the subject is not a living body), the heart-rate value is not transmitted to a memory for storage (step S111).

Figure 12:
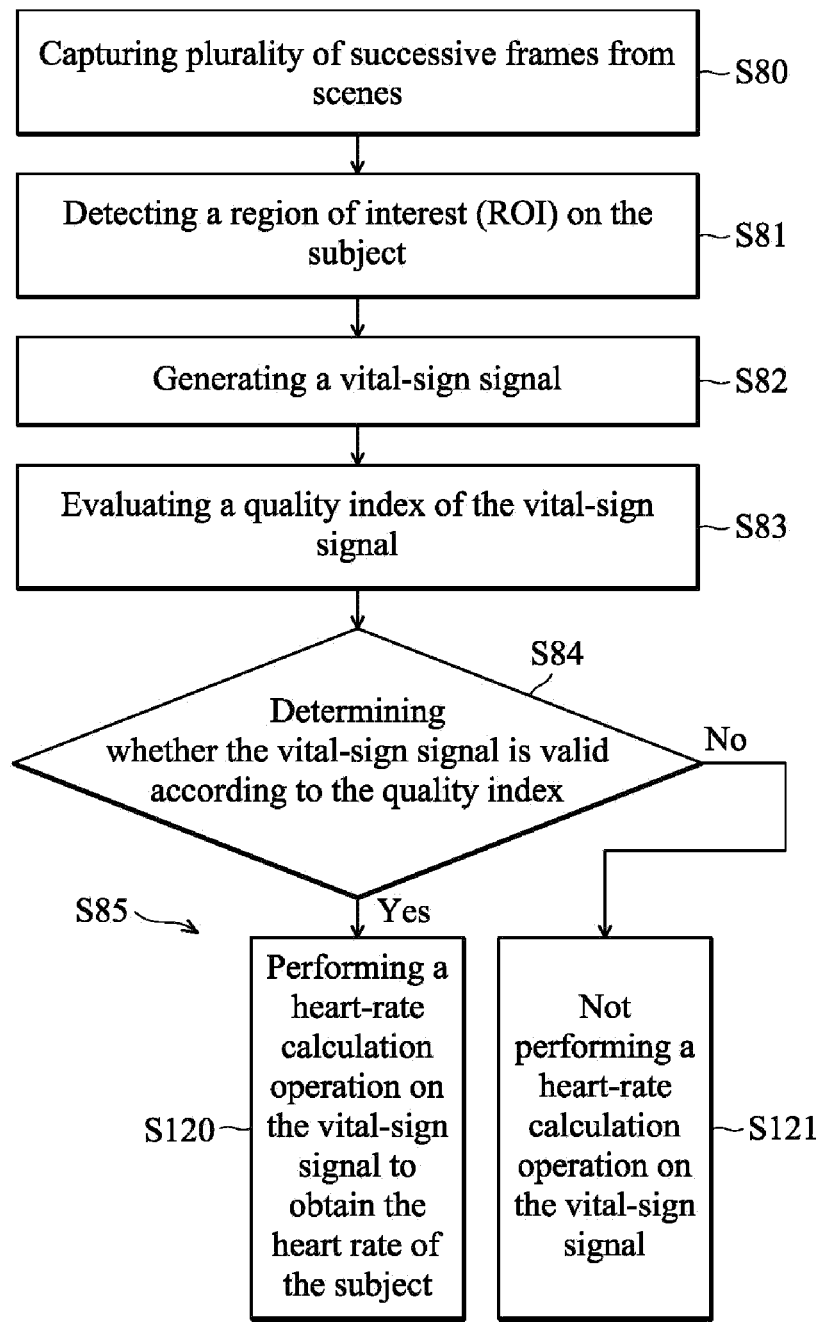

In an embodiment, the calculation of the heart-rate of the subject is performed in the step S85. As shown in FIG. 12, in the step S85, when it is determined that the vital-sign signal is valid (that is the subject is a living body), a heart-rate calculation operation is performed on the vital-sign signal to obtain the heart rate of the subject (step S120). When it is determined that the vital-sign signal is not valid (that is the subject is not a living body), the heart-rate calculation operation is not performed (step S121).

While the invention has been described by way of example and in terms of the preferred embodiments, it is to be understood that the invention is not limited to the disclosed embodiments. On the contrary, it is intended to cover various modifications and similar arrangements (as would be apparent to those skilled in the art). Therefore, the scope of the appended claims should be accorded the broadest interpretation so as to encompass all such modifications and similar arrangements.

The invention claimed is:

1. A determination device for determining whether a subject shown in a plurality of frames captured by an image sensor has a vital-sign feature:
   a processor detecting a region of interest (ROI) on the subject, receiving a plurality of sensing signals related to the ROI, generating a vital-sign signal related to a heart-rate of the subject according to the sensing signals related to the ROI, receiving the vital-sign signal, evaluating a quality index of the vital-sign signal, and determining whether the vital-sign signal is valid according to the quality index to determine whether the subject has the vital-sign feature,
   wherein the valid vital-sign signal indicates that the heart-rate is in a range; and
   wherein the processor detects a peak value of energy of the vital-sign signal in a frequency domain, calculates a first sum of the energy of the vital-sign signal in a first frequency range which contains a frequency value corresponding to the peak value, calculates a second sum of the energy of the vital-sign signal in a second frequency range which contains the first frequency range, calculates a first ratio of the first sum and the second sum, and evaluates the quality index according to the first ratio.

2. The determination device as claimed in claim 1, wherein when the processor determines that the vital-sign signal is valid, the subject has the vital-sign feature.

3. The determination device as claimed in claim 1, wherein when the processor determines that the vital-sign signal is not valid, the subject does not have the vital-sign feature.

4. The determination device as claimed in claim 1, wherein a result of determining whether the subject has the vital-sign feature indicates that the subject is a living body or not.

5. The determination device as claimed in claim 1, wherein the processor further detects a maximum amplitude of the vital-sign signal, calculates an average amplitude of the vital-sign signal, calculates a second ratio of the maximum amplitude and the average amplitude, and evaluates the quality index according to the first ratio and the second ratio.

6. A measurement apparatus for measuring a heart rate of a subject:
   an image sensor to capture a plurality of frames to generate a plurality of sensing signals, wherein a subject is shown in the plurality of frames;
   a processor to detect a region of interest (ROI) on the subject, generate a vital-sign signal related to a heart-rate of the subject according to the sensing signals related to the ROI, evaluate a quality index of the vital-sign signal, and determine whether the subject is a living body according to the quality index to generate a determination signal, wherein the valid vital-sign signal indicates that the heart-rate is in a range; and
   a heart-rate measurement device to receive the determination signal and operate according to the determination signal,
   wherein the heart-rate measurement device comprises:
   a calculator to receive the vital-sign signal and calculate a heart-rate value according to the vital-sign signal; and
   a displayer coupled to the calculator to receive the heart-rate value and controlled by the determination signal,
   wherein when the processor determines that the subject is the living body, the displayer is controlled by the determination signal to show the heart-rate value.

7. The measurement apparatus as claimed in claim 6, wherein the heart-rate measurement device comprises:
   a calculator, controlled by determination signal, to receive the vital-sign signal, calculate a heart-rate value according to the vital-sign signal, and perform a heart-rate statistics operation; and
   wherein when the processor determines that the subject is the living body, the calculator is controlled by the determination signal to apply the heart-rate value in the heart-rate statistics operation.

8. The measurement apparatus as claimed in claim 6, wherein the heart-rate measurement device comprises:
   a calculator to receive the vital-sign signal and calculate a heart-rate value according to the vital-sign signal;
   a transmitter, coupled to the calculator, to receive the heart-rate value and controlled by the determination signal,
   wherein when the processor determines that the subject is the living body, the transmitter is controlled by the determination signal to transmit the heart-rate value to a memory.

9. The measurement apparatus as claimed in claim 8, wherein when the processor determines that the subject is not the living body, the transmitter is controlled by the determination signal not to transmit the heart-rate value to the memory.

10. The measurement apparatus as claimed in claim 8, wherein the transmitter transmits the heart-rate to the memory through wireless communication.

11. The measurement apparatus as claimed in claim 8, wherein the memory is implemented by a cloud storage.

12. The measurement apparatus as claimed in claim 6, wherein when the processor determines that the subject is not the living body, the calculator is controlled by the determination signal not to perform the heart-rate calculation operation on the vital-sign signal.

13. The measurement apparatus as claimed in claim 6, wherein the processor detects a peak value of energy of the vital-sign signal in a frequency domain, calculates a first sum of the energy of the vital-sign signal in a first frequency range which contains a frequency value corresponding to the peak value, calculates a second sum of the energy of the vital-sign signal in a second frequency range which contains the first frequency range, calculates a first ratio of the first sum and the second sum, and evaluates the quality index according to the first ratio.

14. The measurement apparatus as claimed in claim 13, wherein the processor detects a maximum amplitude of the vital-sign signal, calculates an average amplitude of the vital-sign signal, calculates a second ratio of the maximum amplitude and the average amplitude, and evaluates the quality index according to the first ratio and the second ratio.

15. A measurement method:
   capturing a plurality of frames, wherein a subject is shown in the plurality of frames;
   detecting a region of interest (ROI) on the subject;

generating a vital-sign signal related to a heart-rate of the subject according to the sensing signals related to the ROI;

evaluating a quality index of the vital-sign signal; and determining whether the vital-sign signal is valid according to the quality index, wherein the valid vital-sign signal indicates that the heart-rate is in a range, wherein a determination result of determining whether the vital-sign signal is valid is used to control a heart-rate measurement operation;

wherein in the step of evaluating the quality index of the vital-sign signal, a peak value of energy of the vital-sign signal in a frequency domain within a time-interval in which the plurality of frames occur is detected, a first sum of the energy of the vital-sign signal in a first frequency range which contains a frequency value corresponding to the peak value within the time-interval is calculated, a second sum of the energy of the vital-sign signal in a second frequency range which contains the first frequency range is calculated, a first ratio of the first sum and the second sum is calculated, and the quality index according to the first ratio is evaluated.

16. The measurement method as claimed in claim 15, wherein in the step of evaluating the quality index of the vital-sign signal, a maximum amplitude of the vital-sign signal within the time-interval is detected, an average amplitude of the vital-sign signal within the time-interval is calculated, a second ratio of the maximum amplitude and the average amplitude is calculated, and the quality index according to the first ratio and the second ratio is evaluated.

17. A measurement apparatus for measuring a heart rate of a subject:

an image sensor to capture a plurality of frames to generate a plurality of sensing signals, wherein a subject is shown in the plurality of frames;

a processor to detect a region of interest (ROI) on the subject, generate a vital-sign signal related to a heart-rate of the subject according to the sensing signals related to the ROI, evaluate a quality index of the vital-sign signal, and determine whether the subject is a living body according to the quality index to generate a determination signal, wherein the valid vital-sign signal indicates that the heart-rate is in a range; and a heart-rate measurement device to receive the determination signal and operate according to the determination signal, wherein the heart-rate measurement device comprises:

a calculator controlled by the determination signal, wherein when the processor determines that the subject is the living body, the calculator is controlled by the determination signal to perform a heart-rate calculation operation on the vital-sign signal for obtaining a heart-rate value.

* * * * *